United States Patent [19]

Achermann

[11] 4,031,740

[45] June 28, 1977

[54] APPARATUS FOR THERMOANALYTICAL INVESTIGATIONS

[75] Inventor: Heinz Achermann, Uster, Switzerland

[73] Assignee: Mettler Instrumente AG, Zurich, Switzerland

[22] Filed: May 12, 1975

[21] Appl. No.: 576,668

[30] Foreign Application Priority Data

June 25, 1974 Switzerland .......... 8666/74

[52] U.S. Cl. ............................. 73/15 B
[51] Int. Cl.² .......................... G01K 17/00
[58] Field of Search ............ 73/15 B, 17 A, 17 R, 73/190 R; 165/30

[56] References Cited

UNITED STATES PATENTS

| | | | |
|---|---|---|---|
| 3,165,146 | 1/1965 | Smith et al. .................. | 165/30 |
| 3,339,398 | 9/1967 | Barrall et al. .................. | 73/15 |
| 3,456,490 | 7/1969 | Stone .................. | 73/15 |
| 3,491,582 | 1/1970 | Kleiss .................. | 73/17 |
| 3,572,084 | 3/1971 | May .................. | 73/15 |
| 3,680,630 | 8/1972 | Watts .................. | 165/30 |

OTHER PUBLICATIONS

B480,350, Feb. 1976, Regenass et al., 73/190.
Vussallo et al. "Precise Phase Transition of Organic Materials by D.T.A." in Analytical Chemistry vol. 34, 1/62 pp. 132–135.

*Primary Examiner*—Herbert Goldstein
*Attorney, Agent, or Firm*—Werner W. Kleeman

[57] ABSTRACT

A method of, and apparatus for, carrying out thermoanalytical investigations at low temperatures, wherein an article to be investigated is placed in a heating chamber in a furnace and there is ascertained the temperature of the article or a measurement parameter that characterizes the temperature of the article. The temperature in the furnace chamber is brought to a predetermined value by a heating control circuit and a cooling medium is taken from a tank under substantially constant pressure to control the temperature in the furnace chamber. The throughflow of cooling medium is quantitatively controlled to produce a predetermined temperature difference between the furnace chamber and the cooling medium.

13 Claims, 4 Drawing Figures

APPARATUS FOR THERMOANALYTICAL INVESTIGATIONS

BACKGROUND OF THE INVENTION

The present invention relates to a new and improved method of, and apparatus for, carrying out thermoanalytical investigations.

Apparatus for thermoanalytical investigations, especially at low temperatures, have been proposed to the art, and which apparatus is of the type comprising an oven or furnace providing a chamber for receiving a sample or article which is to be investigated, and a device for ascertaining the temperature of the sample or a parameter of the sample which characterises the temperature thereof. The temperature in the sample chamber is controlled to a desired or reference value by a control assembly including a device for pre-setting a desired or reference value. There is further provided a heater for heating the sample chamber and a sensor for measuring the temperature in the sample chamber. Adjacent to but separated from the sample chamber is a chamber for receiving a flowing cooling medium or coolant which is supplied from a cooling medium tank or reservoir.

Such apparatus are used for investigating physical and/or chemical processes as a function of temperature, in other words, for example, apparatus for differential thermal analysis (hereinafter simply conveniently referred to as DTA which is the terminology conventionally employed by those skilled in the art), for thermal mechanical analysis (dilatometer, penetrometer), for thermogravimetry and as calorimeters, to name only some of the most important apparatus of this group and their applications.

Hereinafter for the sake of simplicity reference will be conveniently only made to the case of DTA. It should be expressly understood, however, that all explanations and comments relating to the cooling system and its exchange action with the sample chamber temperature equally apply in principle with respect to the whole of the group of apparatus outline above.

Apparatus for DTA has been proposed for example in U.S. Pat. No. 3,456,490 for effecting DTA at low temperatures. It has been found, however, that when operating with such apparatus there are still some requirements which remain unfulfilled, for example as regards the control or regulation characteristic.

In the proposed apparatus of the prior art either the furnace heater of a heater for heating the cooling medium tank are switched-in in order to carry out a predetermined temperature program under the control of the temperature in the sample chamber. This arrangement allows for only a relatively coarse control or regulation with time-constants which are large (particularly when there are small differences between the reference or desired temperature and the actual temperature), that is to say, substantial delays occur when setting the desired temperature. The result of such delays, for example, is that alterations in the temperature gradient, which can influence the measurement result, can occur more easily in the sample chamber. Additionally, such delays limit the free choice of the program to be used as concerns sensitivity and speed, thereby restricting the capability of the apparatus.

A further difficulty concerns the supply of cooling medium or coolant. Previously proposed apparatus provide a respective cooling medium tank associated with each particular apparatus. This condition had to be fulfilled of necessity because of the operational link between the cooling medium heater and the temperature in the sample chamber. In many cases, however, it is desirable to render the apparatus independent of its own individual source of cooling medium. Thus, for example, it may be more economical for a plurality of apparatus to be connected to a common cooling medium tank, for example by way of a conduit network.

SUMMARY OF THE INVENTION

Accordingly, it is a primary object of the present invention to provide an improved method of, and apparatus for, investigating physical and/or chemical processes in a manner not associated with the aforementioned drawbacks and limitations of the prior art proposals.

Another significant object of the invention aims at the provision of an apparatus which affords the possibility of being operatively connected to a central cooling agent supply, and which in contrast to the heretofore known equipment permits of a considerably increased response speed and accuracy of the regulation of the sample chamber temperature.

Still a further object of the invention is concerned with a new and improved method for effectively and reliably carrying out thermoanalytical inventigations.

In accordance with the present invention there is provided novel apparatus for thermoanalytical investigations at low temperatures, comprising: a furnace having a furnace or sample chamber for receiving an article or sample to be investigated; means for ascertaining the temperature of the article or a parameter of the article that characterises the temperature of the article; means for regulating or controlling the temperature in the furnace chamber to a desired or reference value, said last-mentioned means including means for pre-setting said desired value; means for heating the furnace chamber and a sensor for measuring the temperature in the furnace chamber; a chamber for receiving a flowing cooling medium, said cooling medium chamber being separated from the furnace chamber but being adjacent thereto; supply means connected to the cooling medium chamber for supplying cooling medium thereto; means for quantitatively controlling the throughflow of cooling medium through the cooling medium chamber; a sensor arranged adjacent the cooling medium chamber for measuring the temperature of the cooling medium, and means for pre-setting a desired or reference value of said cooling medium temperature.

The aforedescribed arrangement allows for an advantageous selection of the temperature of the cooling medium or agent, for instance at the output of the cooling path and the maintenance thereof by means of controlling the throughflow of cooling medium. To this end there is advantageously employed a magnetic valve which operates almost without force and which is controlled by the sensor for measuring the temperature of the cooling medium. This arrangement permits of a relatively low power requirement with high response sensitivity of the throughflow control.

Since the cooling medium is delivered to the furnace at low temperature and leaves such furnace only with slightly raised temperature, at the valve there is required a certain expenditure in insulation in order to prevent freezing. This expenditure can be avoided according to a further advantageous aspect of the invention in that the valve is arranged behind the furnace in the direction of flow, and between the furnace and the valve there are provided means for heating the cooling medium.

Continuing, it would be possible to provide for the temperature of the furnace or sample chamber and that of the cooling medium two separate, for instance time-controlled reference value programs. However, the means for pre-setting the reference or desired value of the furnace chamber temperature is advantageously linked with that for pre-setting the reference or desired value of the cooling medium temperature. In this way it is sufficient to fix only for the furnace chamber temperature a reference value or a reference value program respectively, and the reference value of the cooling medium temperature then automatically follows that of the furnace chamber temperature, and the difference between both values can be constant or variable, for instance depending upon the working temperature range.

There is also possible a free selection of the cooling medium. Thus, it is for instance conceivable to work with cold air or cold nitrogen gas, the gas being conducted through a cold liquid medium for assuming the desired cooling temperature. A preferred exemplary embodiment of the apparatus of this development contemplates generating cooling medium vapors (e.g. from liquid nitrogen) and is characterized by the provision of means for maintaining constant the pressure of the vaporized cooling medium in the reservoir or supply means containing the liquid cooling medium. This constitutes a particularly favorable arrangement because the operation against a (at least approximately) constant pressure renders possible a rapid, good reproducible regulation of the temperature in the furnace or sample chamber.

The pressure regulation or control is advantageously constructed such that the means for maintaining constant the pressure incorporates a heating device and a pressure measuring cell influencing its heat delivery or output and which encompasses a diaphragm barometer with inductive scanning of the diaphragm movement. This construction permits of an accurate, very sensitive regulation of the desired pressure in the vapor phase of the cooling medium. The heating device preferably encompasses a hollow constructed heating element incorporating a perforated sheet metal member and a heating conductor operatively connected therewith. With this constructional manifestation it is possible to realize a good heating efficiency with short response time of the heating with low temperature differences between the heating body and the cooling medium or agent.

When working with cooling medium vapors obtained from the liquid phase it is particularly desired —especially in consideration of extensive trials— to be protected against unexpected failure of the cooling medium supply. An advantageous further constructional manifestation of the invention therefore contemplates the provision of means for signalling a critical filling height of non-vaporized liquid.

According to another aspect of the invention there is contemplated a method for carrying out thermoanalytical investigation at low temperatures, wherein an article or simple to be investigated is placed in a furnace or sample chamber in a furnace; there is ascertained the temperature of the article or a measurement parameter that characterises the temperature of the article; the temperature in the furnace chamber is brought to a predetermined value by a heating regulating or control circuit; cooling medium is taken from a reservoir or tank under substantially constant pressure to control the temperature in the furnace chamber; and the throughflow of cooling medium is quantitatively controlled to produce a predetermined temperature difference between the furnace chamber and the cooling medium.

BRIEF DESCRIPTION OF THE DRAWINGS

A method and apparatus according to the present invention will now be described by way of example with reference to the accompanying drawings, wherein.

DETAILED DESCRIPTION OF THE INVENTION

Figure 1:
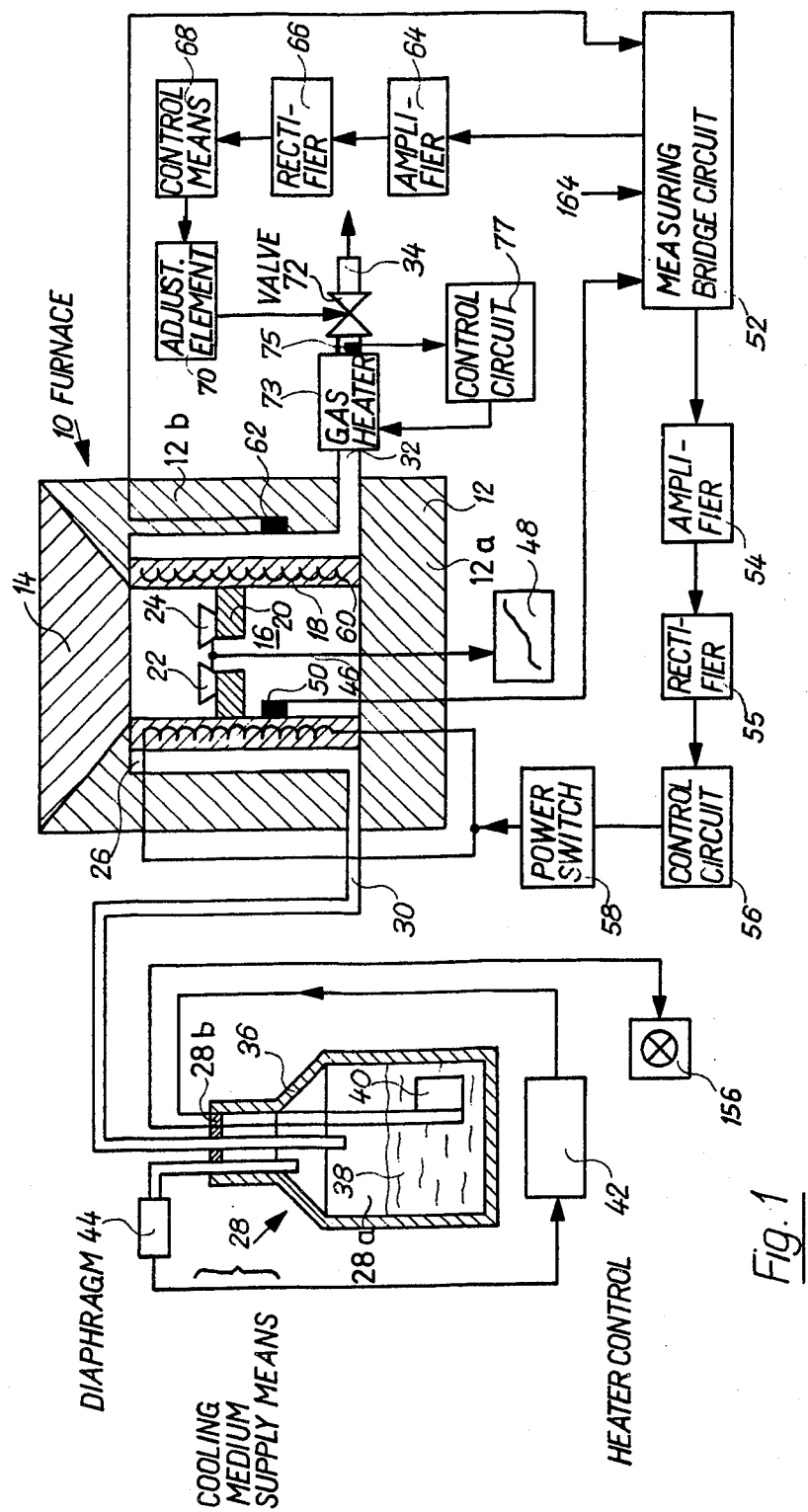
FIG. 1 shows a general view of apparatus for differential thermal analysis, partly in cross-section and partly in diagrammatic form.

Referring firstly to the arrangement of FIG. 1, the apparatus illustrated by way of example has a furnace 10, shown in sectional view, which substantially comprises a body 12 formed by a solid floor or bottom 12a and side walls 12b, and a cover or closure member 14 which closes the body 12 at its upper end, so as to be heat-tight and gas-tight. A chamber or compartment 16 is formed in the interior of the furnace 10 and serves for receiving a sample or article which is to be investigated. The chamber 16 is usually referred to herein as a sample-receiving chamber or furnace chamber. Surrounding the sample-receiving chamber 16 is a furnace wall 18 supporting two mounting means 20 for respectively mounting or supporting a sample holder vessel 22 and a reference substance holder vessel 24. The furnace wall 18 is surrounded at the outside thereof by an annular chamber 26 through which there can flow a gaseous cooling medium or agent. The cooling medium is removed from a reservoir or tank 28 constituting cooling medium-supply means and supplied to the annular chamber 26 by way of a feed conduit 30. From the annular chamber 26 the cooling medium is discharged by way of a discharge or withdrawal conduit 32 and vented into the atmosphere by way of an outlet 34.

The reservoir or tank 28 comprises an insulated, hermetically sealed vessel or container, such as a Thermos or Dewar vessel 36, and in use contains a cooling medium such as typically liquid nitrogen 38. Immersed in the liquid nitrogen 38 is a heating element 40, the thermal output of which can be controlled by means of a control or regulating circuit 42 with the aid of a diaphragm barometer 44 in such a manner that the vapor pressure of the nitrogen which is evaporated in the vessel 36 by the heat dissipated by the heating element 40 is maintained at a substantially constant value of, for example, 0.6 atmospheres.

The temperature of the sample and the reference substance are ascertained by means of a pair of thermocouples 46 which are connected in opposing electrical relationship and which detect the temperature at the vessels 22 and 24. The temperatures are graphically displayed by a suitable recorder or recording means 48. The temperature in the sample-receiving chamber 16 is detected by a temperature sensor 50 having a resistor, schematically indicated by reference character 50a (FIG. 4), which lies in one branch of a measuring bridge circuit 52, as will be explained more fully hereinafter with reference to FIG. 4. In the measuring bridge circuit 52 the resistance of the sensor 50 is compared with the respective desired or reference value of the temperature in the sample-receiving chamber 16. The difference or differential signal is amplified in an amplifier 54 and transmitted to a rectifier or rectifier arrangement 55, a control circuit 56 and a power switch 58, and then used to influence the operating time of a resistance heater 60 which is embedded in the wall 18 of the furnace 10.

Adjacent the annular chamber 26 is a further temperature sensor 62 which is arranged in the side wall 12b of the body 12 of the furnace 10, as best seen by referring to FIG. 1. The temperature sensor 62 has a resistor, also schematically indicated by reference character 62a in FIG. 4, which is arranged in a further branch of the measuring bridge circuit 52 and whose resistance is also compared with a respective desired or reference value. The corresponding differential signal is similarly amplified in amplifier 64 and transmitted to a rectifier 66 to operate a control means or circuit 68 which influences an adjusting member 70 to control the position of a solenoid or magnetic valve 72. Depending upon the degree of opening of the valve 72, a greater or lesser amount of cooling medium will flow through the annular chamber 26. The valve 72 thus will be operable to control the throughflow of cooling medium through the apparatus as a function of the temperature measured by the temperature sensor 62.

A gas throughflow heater 73 of conventional construction is incorporated into the conduit 32 between the furnace 10 and the solenoid valve 72. The heater 73 encompasses a ceramic body with heating spirals embedded therein, the gas flowing directly over the heating spirals or wires. A temperature sensor 75 measures the temperature of the gas after leaving the heater 73 and accordingly controls a control circuit 77 which operates to regulate the length of time of operation of the heater 73. The control or regulating action is set such that the cooling medium reaches the solenoid valve 72 at a temperature of about 30° C. The increase in the volume of the gas caused by the intermediate heating thereof (by means of the heater 73) is in no way detrimental since the control circuit which is regulated by the temperature sensor 62 is the decisive factor as regards the opening of the valve 72. If the gas were not heated in the described manner between the furnace 10 and the valve 72 insulation would be required in the valve 72 in order to prevent freezing inasmuch as the cooling medium is supplied to the furnace 10 at a low temperature and again leaves the furnace at only a slightly higher temperature. This can be avoided by the valve 72 being arranged downstream of the furnace 10 in the direction of flow of the cooling medium, the heater 73 being beneficially provided between the furnace 10 and the valve 72 for heating the cooling medium.

Figure 2:
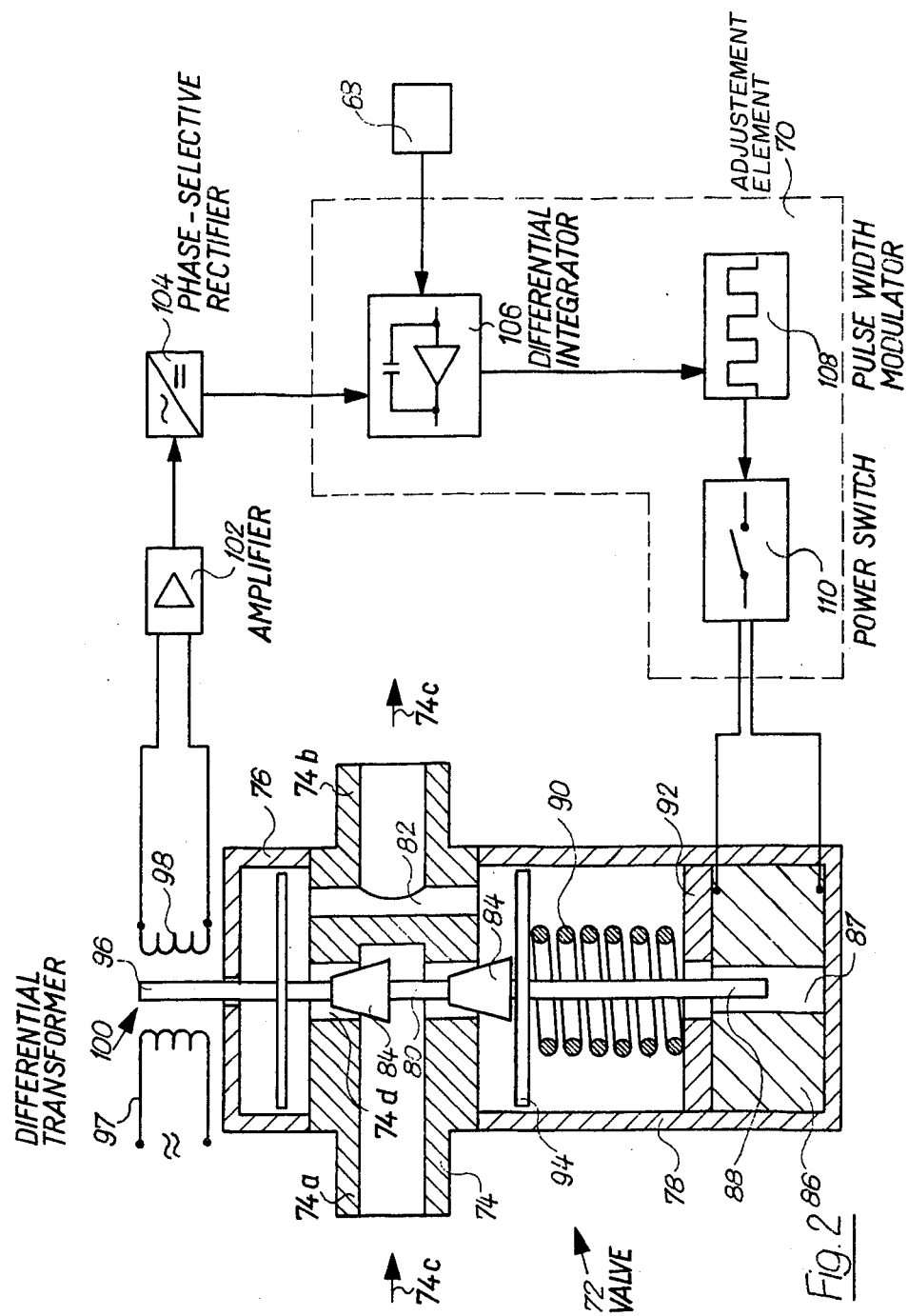
FIG. 2 illustrates a valve for controlling the throughflow of cooling medium in the apparatus of FIG. 1.

FIG. 2 illustrates the valve 72 in greater detail. This valve 72 has a valve body 74 which is closed at its upper and lower ends by respective caps or cap members 76 and 78. The valve body 74 contains an inlet connection 74a and outlet connection 74b for the cooling medium which flows in the direction indicated by the arrows 74c, a first radially directed bore 74d for a valve spindle 80, and a further radial bore 82 laterally adjacent the first bore 74d for the gas flow. The spindle 80 is provided with two valve members or valve plates 84 which are of identical construction and which, in conjunction with the radial bore 74d, control the throughflow of gas depending upon the position of the spindle 80.

The lower cap or cap member 78 encloses an annular pulling or traction electromagnet 86 having a bore 87 into which there extends one end 88 of the spindle 80. A compression or pressure spring 90 bears at one end against an annular or ring-shaped flange 92 in the cap member 78 and at the other end against a collar 94 which is fixedly connected to the spindle 80. This spring 90 thus urges the spindle 80 and valve members 84 upwardly towards the position in which the valve 72 is closed. The upper end portion or end 96 of the spindle 80 extends in the form of a vane member or core into the space between two coils or windings 97 and 98 and forms therewith a differential transformer 100 for sensing the valve movement. Depending upon the position of the vane member 96, the coil 98 delivers an alternating-current voltage output signal which is amplified in an amplifier 102 and applied to a phase-selective rectifier 104. At the output of the rectifier 104 the signal is transmitted to the adjustment element or arrangement 70 which comprises a difference or differential integrator 106, a pulse-width modulator 108 and a power switch 110. The output of the adjustment element 70 is connected to the electromagnet 86. This closed control circuit ensures that the valve 72 operates in a substantially flutter-free manner, and the control voltage displacement characteristic of the electromagnet 86 is made virtually linear. The construction of the valve 72 with two valve members or plates 84 against which acts the gas pressure in opposite directions results in the fact that only small displacement forces are required for changing the valve position. Consequently, the valve has low power requirements and possesses a high degree of sensitivity of response as regards controlling the throughflow of cooling medium.

A safety valve of conventional construction (not shown) ensures that no dangerous excess pressure can build up in the system.

Figure 3:
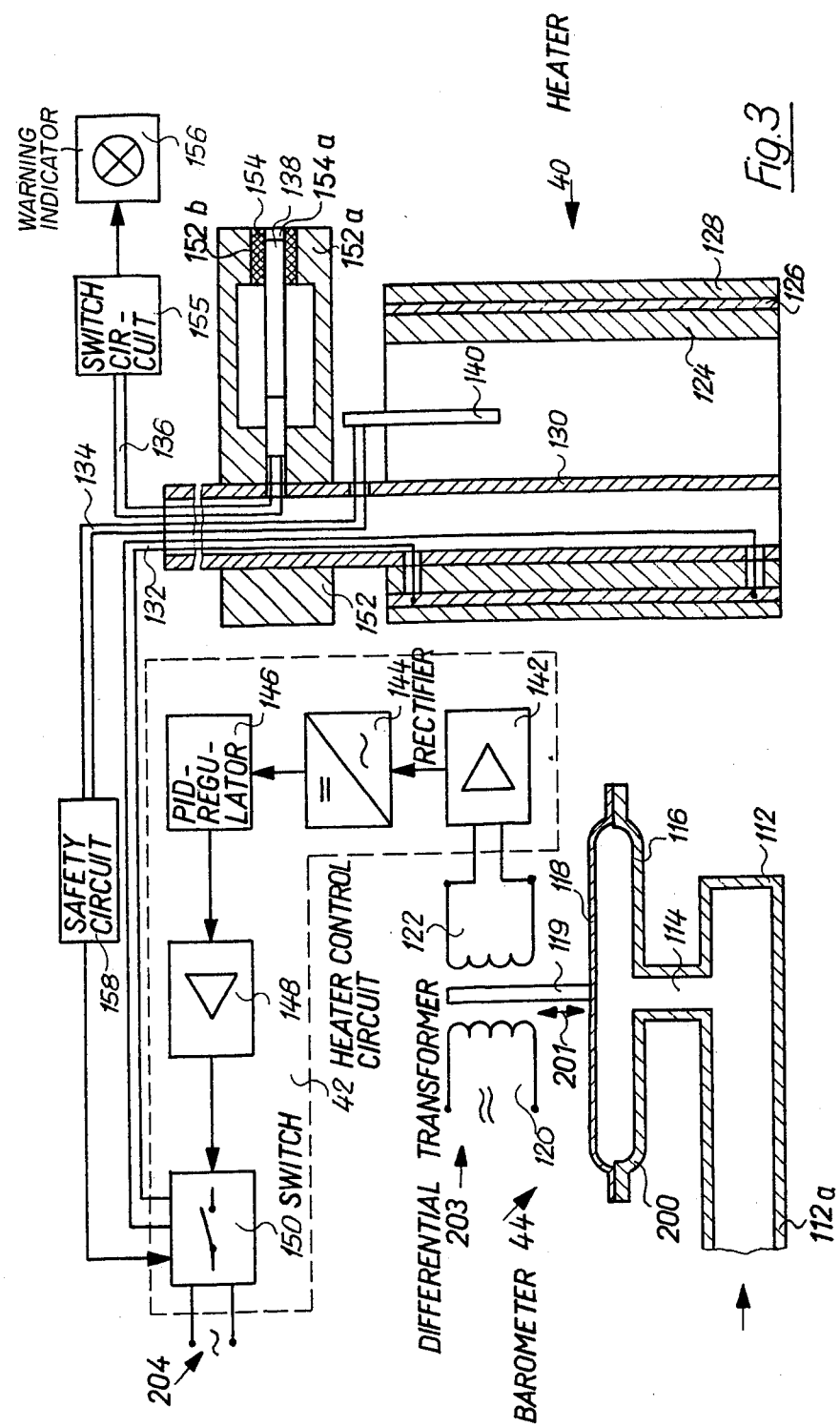
FIG. 3 illustrates a pressure measuring cell in the cooling medium tank and the heating element thereof for the apparatus of FIG. 1.

FIG. 3 shows details of the control circuit for the heating element or heater 40 and which control circuit includes the barometer 44. This barometer 44 comprises a tube member 112 which is open at one end 112a and is secured to the reservoir or tank 28 (not shown in FIG. 3) and projects into the vapor space 28a therein (see FIG. 1). A pressure measuring member 200 of substantially circular cross-section and having a lower wall 116 and an upper wall 118 is connected with the tube member 112 by way of a short connecting piece or pipe 114, the pressure-measuring member 200 being shown in diametral cross-section in FIG. 3. The upper wall 118 acts as a diaphragm and is yieldable or displaceable in the direction of the double-headed arrow 201 under the influence of the prevailing pressure applied thereto by way of tube member 112 and connecting piece 114. A metal vane or core 119 is fixed on the upper wall 118 defining the diaphragm and projects into a gap between two coils or windings 120 and 122. The vane 119 and the coils 120 and 122 form a differential transformer 203 for inductively sensing the diaphragm movement, and output signals of which (at coil 122) constitute a measure of the degree of deflection or movement of the upper diaphragm wall 118 and thus of the pressure of the cooling medium vapor in the tank or reservoir 28. These signals are transmitted to the control circuit 42 where they are operable to control the thermal output of the heater 40.

The heater 40 is a substantially hollow-cylindrical structure which comprises three components: an aluminium perforated plate 124 bent into a substantially round cylindrical configuration, a heating foil or print 126 which is wound thereon (heating foil 126 being constituted by a heat conductor pressed onto a plastic film), and an aluminium foil shell or jacket 128 which is wound around the heating foil 126. The heater 40 is secured to a tube or tube member 130 which is fitted into the cover 28b of the reservoir of tank 28 and which carries in its interior electrical leads 132, 134 and 136 for the heating foil 126 and for two platinum sensors 138 and 140 which will be considered more fully hereinafter.

The heat or thermal output of the heater 40 is controlled as follows: the signal from the coil 122 is transmitted by way of an amplifier 142 and a phase-selective rectifier 144, to a PID-controller or regulator 146, i.e. a controller having a proportional-integral-differential characteristic. The control signal produced by the controller or regulator 146 is amplified in amplifier 148 and controls a switch 150 which, through the agency of the electrical leads 132, connects the heating foil or print 126 to the power supply 204 or disconnects it therefrom. The arrangement is so set that the pressure in the gas phase in the tank 28 remains virtually constant at 0.6 atmospheres. This constant pressure provides the advantages that operation against a (at least approximately) constant pressure provides for a rapid and readily reproducible control action as regards the temperature in the chamber 16.

The configuration of the heater 40 as a cylindrical perforated plate 124 with heating foil 126 wound therearound, due to the good heat-exchange contact with the liquid nitrogen, ensures that the temperature difference between the latter and the heater 40 does not exceed about 3° to 4° C, and in this way local overheating can be avoided. The outer jacket 128, besides acting as a mounting for the heating foil 126 and for heat transfer, also protects the heating foil 126 from mechanical damage, for example upon assembly or dismantling.

Associated with the heater 40 are two level indicators, each of which comprise one of the above-mentioned platinum sensors 138 and 140. The first sensor 138 is fitted in a holder 152 secured to the tube or tube member 130. The end 152a of the holder 152 remote from the tube 130 is apertured i.e. provided with a bore 152b and a plastic sleeve 154 is carried in this bore. Supported in the bore 154a of the sleeve 154 is the end of the active part of the sensor 138, the sleeve 154 thus providing thermal insulation. As soon as the level of liquid nitrogen in the reservoir or tank 28 falls to such an extent that the sensor 138 is no longer surrounded by liquid nitrogen, then the resistance of the sensor 138 changes due to a self-heating action, and the rise in voltage resulting therefrom causes operation of a circuit 155 to switch on a signaling means, such as a warning indicator or lamp 156, to indicate that a critical level of unevaporated liquid has been reached in the reservoir or tank 28. This provides protection from an unexpected break in the supply of cooling medium, which protection may be particularly desirable when carrying-out long-duration experiments.

The second level indicator comprising the sensor 140 is arranged at a lower depth in the reservoir or tank 28 but operates in a similar manner. The sensor 140 is mechanically connected to the perforated plate 124. If the level of liquid nitrogen in the tank falls below the sensor 140, then the heater 40 is switched off by the action of a safety circuit 158.

Figure 4:
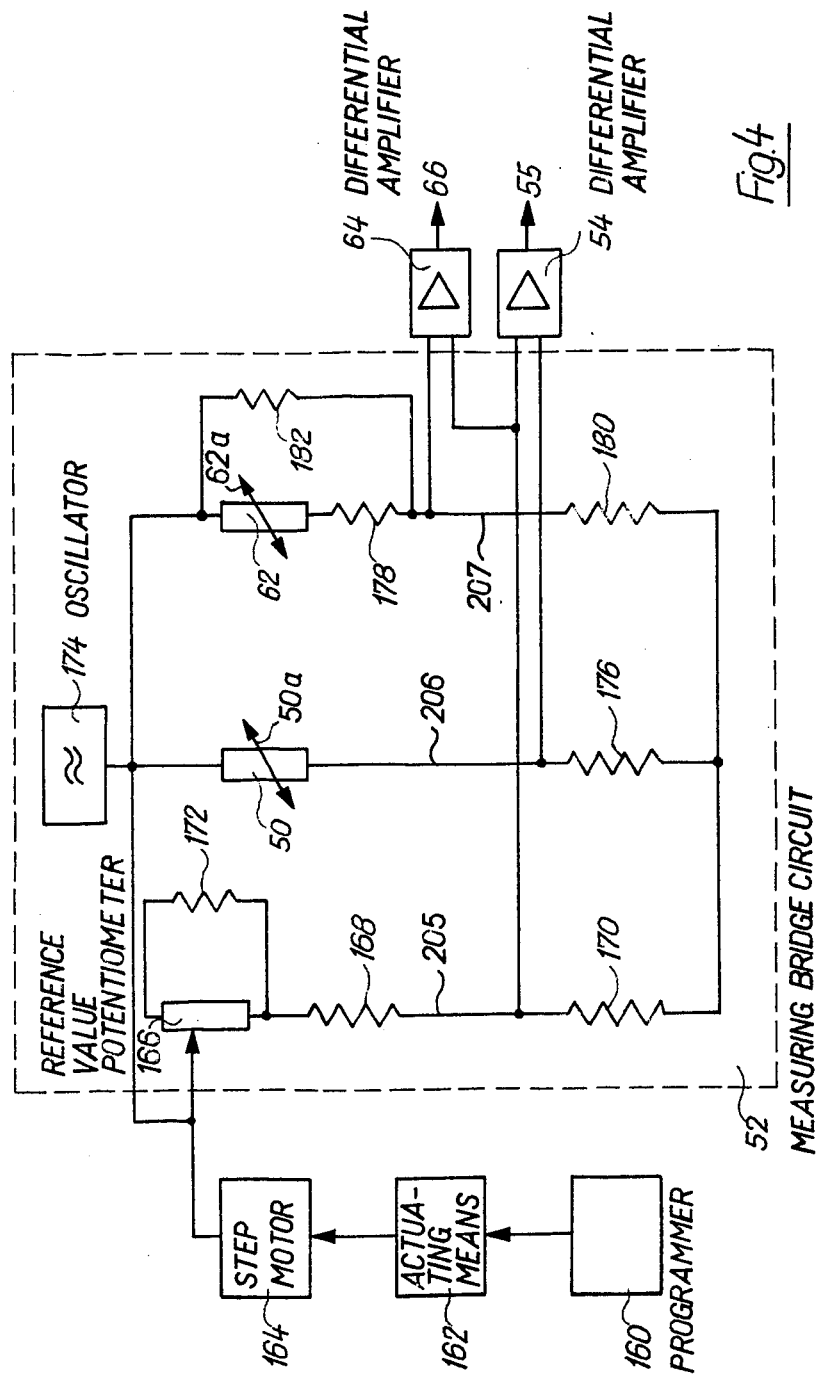
FIG. 4 shows a part of the electrical circuit of the apparatus.

FIG. 4 shows the connection or coupling between the controls or regulators for the temperatures of the sample-receiving chamber 16 (sensor 50) and the cooling medium (as measured by sensor 62), by means of the measuring bridge circuit 52. A control device (programmer) 160 controls the actuating means 162 for a stepping motor 164 which adjusts a desired or reference value potentiometer 166. The potentiometer 166 is arranged in series with two fixed-value resistors 168 and 170 and in parallel with a further fixed resistor 172, thereby forming a first branch of the measuring bridge circuit 52. This measuring bridge circuit 52 is supplied with an alternating-current voltage by an oscillator 174. A second branch of the bridge circuit 52 includes the temperature sensor 50 connected in series with a fixed-value resistor 176. The parallel resistor 172 serves for linearisation of the characteristic curve of the platinum sensor 50 for the display means (not shown) for displaying the temperature of the chamber 16.

The two voltages of the first and second branches 205 and 206 of the measuring bridge circuit 52 are applied to the differential amplifier 54 and control the furnace heater 60 (see the above description referring to FIG. 1).

A third branch 207 of the measuring bridge circuit 52 includes the sensor 62. Two fixed-value resistors 178 and 180 are connected in series with the sensor 62, while a fixed-value resistor 182 is arranged in parallel with such sensor 62. The voltage across the first branch 205 and third branch 207 of the measuring bridge circuit 52 are applied to the differential amplifier 64 and control the opening of the magnetic or solenoid valve 72 (see the preceding description relating to FIGS. 1 and 2).

It will be apparent therefore that the cooling control circuit is controlled by the desired or reference value (as set at the reference value potentiometer 166) of the temperature in the sample-receiving chamber 16. Different combinations can be provided depending upon the resistance values of the resistors 178, 180 and 182. A simple possibility would be to predetermine a constant temperature difference ΔT between the desired or reference value of the temperature in the sample-receiving chamber 16 and the temperature of the cooling medium. In the present embodiment however the arrangement is such that ΔT also increases with increasing temperature in the sample-receiving chamber 16. Thus a ΔT of about 20° C corresponds for example to a desired value of the temperature in the sample chamber of −150° C, while a ΔT of about 80° corresponds to a desired value of +500° C. The variation in ΔT affords some advantages as regards the mode of operation of the apparatus. It ensures that the valve 72 responds quickly at high temperatures, that is to say, it opens rapidly, but is fully open only at very low temperature. On the one hand, this provides for very rapid cooling with high initial temperatures but, on the other hand, the consumption of cooling medium is kept relatively small at lower temperatures. In addition, when designing the measuring bridge circuit 52 (selection of the resistors 178, 180 and 182), there can be taken into account the apparatus constants and the envisaged temperature programs in such a way that the desired or reference temperatures for the cooling medium in each case are lower than those values which result from "natural" cooling, for example as a result of heat radiation loss from the side wall of the furnace (preventing heat build-up or undesired temperature gradients in the furnace).

The above-described arrangement which permits of extremely rapid operation makes it possible, for example, without substantial loss of time to change the sample at room temperature. Quite apart from the fact that this makes handling of the apparatus very much more simple, the troublesome formation of condensate water in the sample-receiving chamber 16 may be virtually completely eliminated.

Due to the time-saving mode of operation over a wide temperature range (for example from −150° to +600° C), the use of the apparatus is not limited to the conventional field of scientific laboratory work, but the apparatus also can be employed in many areas of industrial use (for example production control), where in many cases it affords an advantageous alternative to other forms of apparatus, for example gas chromatographic devices. Also, the above-described apparatus can be connected to a central cooling medium source, instead of requiring its own source, as with previously proposed apparatus.

Any suitable cooling medium can be used, for example cold air or cold nitrogen gas, the gas being passed through a cold liquid medium to bring it to the desired cooling temperature.

It will be noted that in the above-described apparatus, the means for pre-setting the desired or reference value of the temperature in the sample-receiving chamber 16 are connected to the means for pre-setting the desired or reference value of the cooling medium temperature, so that it is sufficient to establish a desired or reference value or a desired or reference value program only as regards the sample-receiving chamber termperature, and the references or desired value of the cooling medium temperature then automatically follows that of the sample-receiving chamber temperature; the difference between the two values can be constant or variable, for example depending on the temperature range in which operation is to occur. In an alternative but less advantageous construction however, it would be possible to provide two separate desired-value programs which are, for example, time-controlled, for the temperature of the sample-receiving chamber 16 and the temperature of the cooling medium.

While there is shown and described present preferred embodiments of the invention, it is to be distinctly understood that the invention is not limited thereto, but may be otherwise variously embodied and practiced within the scope of the following claims.

What is claimed is:

1. An apparatus for thermoanalytical investigations at low temperatures, comprising:
    a. a furnace having a furnace chamber for receiving an article to be investigated;
    b. means for ascertaining the temperature of the article or a parameter of the article that characterizes the temperature of the article;
    c. means for controlling the temperature in the furnace chamber to a desired value following a predetermined temperature versus time program, said controlling means including
        1. means for pre-setting said desired value;
        2. means for heating the furnace chamber; and
        3. a sensor cooperating with the furnace for measuring the temperature in the furnace chamber;
    d. a hollow cooling medium chamber having an inlet and an outlet through which flows a cooling medium, said cooling medium chamber being separated from the furnace chamber but being disposed adjacent thereto and adjacent to said heating means;
    e. supply means connected to the cooling medium chamber for supplying cooling medium thereto; and
    f. means for controlling the temperature of the cooling medium near said outlet to a desired value following a predetermined temperature versus time program, said controlling means including
        1. means for pre-setting said desired value;
        2. a sensor cooperating with the cooling medium chamber for measuring the temperature of the cooling medium near said outlet; and
        3. means for quantitatively controlling the throughflow of cooling medium through the cooling medium chamber.

2. The apparatus according to claim 1, wherein said means for controlling the throughflow of cooling medium includes a solenoid valve which operates virtually without force and which is controlled by said sensor for measuring the temperature of the cooling medium.

3. The apparatus according to claim 2, wherein said solenoid valve is arranged downstream of the furnace in the direction of flow of the cooling medium, and means for heating the cooling medium provided between said furnace and said solenoid valve.

4. The apparatus according to claim 1, wherein said means for controlling the desired value of the furnace chamber temperature is connected to said means for pre-setting the desired value of said cooling medium temperature.

5. The apparatus according to claim 1, wherein said supply means comprises a cooling medium tank for containing a vaporisable liquid constituting a vaporisable cooling medium, and means for maintaining substantially constant the vapor pressure of evaporated cooling medium in the tank.

6. The apparatus according to claim 5, wherein said means for maintaining the vapor pressure substantially constant comprises a heater means and a pressure measuring means operable to control the thermal output of said heater means.

7. The apparatus according to claim 6, wherein the heater means comprises a hollow heating element incorporating a perforated plate member and a heating conductor connected thereto.

8. The apparatus according to claim 5, further including means for signalling when there has been reached a critical level of unevaporated liquid in the tank.

9. A method for carrying out thermoanalytical investigations at low temperatures, comprising the steps of:
    a. placing an article to be investigated in a heating chamber in a furnace;

b. detecting the temperature of the article or a measurement parameter that characterises the temperature of the article;
c. bringing the temperature in the furnace chamber, following a temperature versus time program, to a predetermined value by a heating control circuit;
d. removing cooling medium from a tank under substantially constant pressure and feeding such to the furnace in order to control the temperature in the furnace chamber; and
e. quantitatively controlling the throughflow of the cooling medium through the furnace between a cooling medium inlet and a cooling medium outlet to produce a predetermined temperature difference between the furnace chamber and the cooling medium, the throughflow control of the cooling medium including measuring the temperature of said cooling medium near the region of the cooling medium outlet.

10. The method according to claim 9, including the step of bringing the temperature in the furnace chamber to predetermined values in accordance with a given program.

11. The method according to claim 9, wherein the cooling medium used is an evaporated liquid and maintaining substantially constant the vapor pressure in the tank by a further heating control circuit.

12. The method according to claim 11, including the step of monitoring the level of unevaporated liquid in the tank.

13. The method according to claim 9, wherein said predetermined temperature difference is determined by the predetermined temperature in the furnace chamber.

* * * * *